United States Patent [19]

Bartels

[11] Patent Number: 4,960,920

[45] Date of Patent: Oct. 2, 1990

[54] PROCESS FOR THE PREPARATION OF α-AMINOALKYLPHOSPHONIC ACIDS AND OF α-AMINOALKYL-PHOSPHINIC ACIDS

[75] Inventor: Günter Bartels, Braunschweig, Fed. Rep. of Germany

[73] Assignee: Hoechst Aktiengesellschaft, Frankfurt an Main, Fed. Rep. of Germany

[21] Appl. No.: 348,144

[22] Filed: May 2, 1989

Related U.S. Application Data

[63] Continuation of Ser. No. 75,248, Jul. 16, 1987, abandoned, which is a continuation of Ser. No. 807,455, Dec. 10, 1985, abandoned.

[30] Foreign Application Priority Data

Dec. 12, 1984 [DE] Fed. Rep. of Germany ....... 3445300

[51] Int. Cl.$^5$ .............................. C07F 9/40; C07F 9/46
[52] U.S. Cl. ...................................... 558/170; 562/15
[58] Field of Search ........................... 562/15; 558/170

[56] References Cited

U.S. PATENT DOCUMENTS

| 2,754,320 | 7/1956 | Johnston | 558/170 |
| 2,953,595 | 9/1960 | Rauhut et al. | 562/15 |
| 3,980,614 | 9/1976 | Noetzel et al. | 562/15 |
| 3,980,615 | 9/1976 | Noetzel | 562/15 |
| 4,105,689 | 8/1978 | Auer et al. | 562/15 |
| 4,886,628 | 12/1989 | Kleiner | 562/15 |

FOREIGN PATENT DOCUMENTS 367109  1/1973  U.S.S.R. ............................ 558/179

OTHER PUBLICATIONS

The Merck Index, 6th ed. (1952), pp. 1060 and 1061.
Organic Reactions, 3 (1946), p. 267 ff., "The Hoffmann Reaction", p. 268 (Wallis et al.).
Rachon et al., "Aminophosphonic Acids; Hofmann Degradation of Carboxamides-A New Method of the Preparation of Alpha–Aminophosphonic Acids", Z. Chem., 14, No. 4, pp. 152-154 (1974).
Chemical Abstracts, 81, No. 63728m, p. 484 (1974).
Article by L. Maier, "Advances in the Chemistry of Aminophosphinic Acids" in the journal Phosphorus and Sulfur, 1983, vol. 14, pp. 295-322.
Hofmann Degradation and Bromination of Amides derived from Phosphonoacetic Acid (Tetrahedron Letters, No. 52, pp. 5201-5202, 1973).
J. Org. Chem, 23, pp. 1888-1886) (1958).

*Primary Examiner*—J. E. Evans
*Attorney, Agent, or Firm*—Curtis, Morris & Safford

[57] ABSTRACT

α-Aminoalkylphosphonic and α-aminoalkylphosphinic acids of the formula I

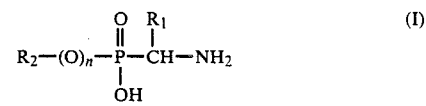

where
n=1 or 0,
$R_1$=H, $CH_3$ or $CH_2$—$C_6H_5$
$R_2$=H (for n=1) and also=alkyl or phenyl (for n=0)

are prepared by Hofmann deradation from compounds of the formula II

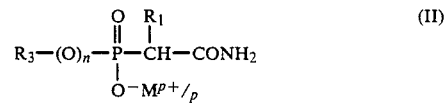

wherein
n and $R_1$ have the same meaning as in formula I,
$R_3$=alkyl (for n=1), alkyl or phenyl (for n=0), and
$M^{p+}$=p—valent cation, with subsequent working up in the known manner.

Some of the compounds I are biologically active, and some are intermediates for the preparation of biologically active compounds.

12 Claims, No Drawings

PROCESS FOR THE PREPARATION OF α-AMINOALKYLPHOSPHONIC ACIDS AND OF α-AMINOALKYLPHOSPHINIC ACIDS

This application is a continuation of application Ser. No. 07/075,248, filed July 16, 1987, now abandoned, which is a continuation of Ser. No. 807,455 filed Dec. 10, 1985, now abandoned.

The invention relates to a process for the preparation of α-aminoalkylphosphonic and of α-aminoalkylphosphinic acids of the formula I

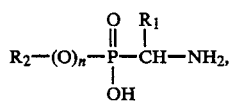

where
n = 1 or 0,
$R_1$ = H, $CH_3$ or $CH_2$-$C_6H_5$, and
$R_2$ = H (for n = 1) and also
= alkyl or phenyl (for n = 0).

For n = 1 α-aminoalkylphosphonic acids are represented, and for n = 0 α-aminoalkylphosphinic acids.

Some of the compounds are biologically active such as, for example, aminomethylphosphonic acid

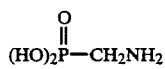

which is known to have a herbicidal and plant-growth regulating activity; some of the compounds may also be processed further to form biologically active substances (cf. the article by L. Maier entitled "Advances in the Chemistry of Aminophosphinic Acids" in the journal "Phosphorus and Sulfur", 1983, Vol. 14, pages 295–322, in particular 317–320). Although this article is mainly concerned with aminophosphinic acids (as is already evident from the title), nevertheless aminophosphonic acids are also dealt within it.

For this reason part A (Preparation of aminophosphinic acids) on pages 296–313 of this article describes not only a number of known processes for the preparation of aminophosphinic acids, but also various methods for the preparation of aminophosphonic acids. In principle the compounds with the above formula I can also be obtained by this process.

A method not included in those quoted in the said article is the method described in the paper by M. Soroka and P. Mastalerz "Hofmann Degradation and Bromination of Amides derived from Phosphonoacetic Acid" (Tetrahedron Letters No. 52, pages 5201–5202, 1973) for the preparation of some special α-aminoalkylphosphonic acids by Hofmann degradation and acidic hydrolysis of the esters of various phosphonocarboxylic acid amides.

By the Hofmann degradation carboxylic acid amides can be converted into the amines with one C atom less by treatment with chlorine or bromine in an alkaline medium (in which the corresponding hypohalogenites are formed) (cf., for example, Organic Reactions 3(1946), page 267 ff., "The Hofmann Reaction", in particular page 268); the following reaction equation is specified for the Hofmann degradation (with bromine as the halogen):

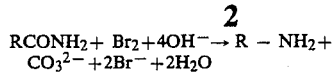

(R = organic radical)

The Hofmann degradation reactions described in the paper by M. Soroka and P. Mastalerz at the place cited above may be represented by the following system of formulae:

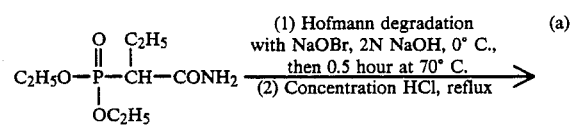

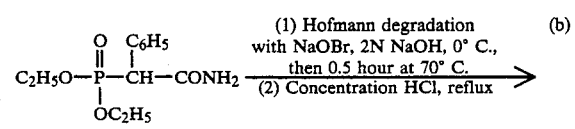

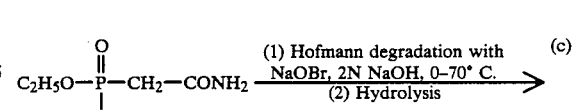

The yields of the corresponding α-aminoalkylphosphonic acids are said in this case to be around 70 to 80% of the theoretical yield.

If the C atom linked to the phosphorus is not substituted or is substituted by other groups, phosphonocarboxylic acid derivatives (and virtually no halogen-free amines) are said to be primarily produced in the Hofmann degradation:

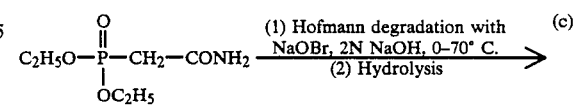

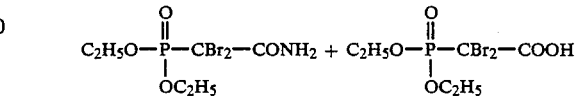

If 2 mol of NaOBr are used here instead of the one mol otherwise usual for the Hofmann degradation, the yield of the compound diethyl aminocarbonyldibromomethylphosphonate

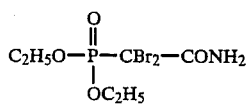

is said to be up to 75%.

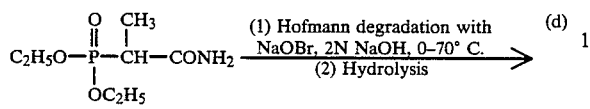

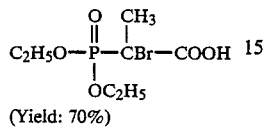

(Yield: 70%)

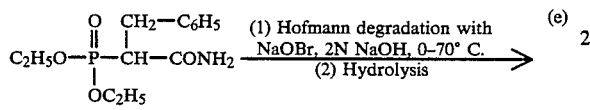

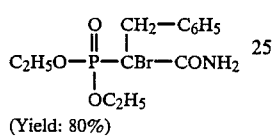

(Yield: 80%)

If the hydrolysis proceeds further, the phosphonic ester groups in the products of reactions (c), (d) and (e) are of course also converted into the OH groups.

As our own experiments have shown, even if the NaOBr is replaced by NaOCl, virtually no halogen-free amine is produced in the reaction (c) mentioned above:

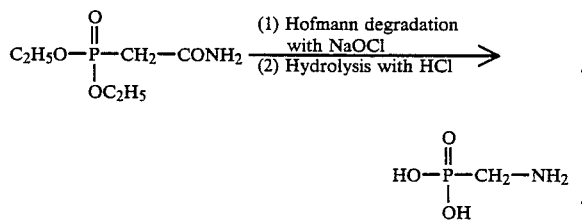

In an analogous manner the ethyl (aminocarbonylmethyl) methylphosphinate also fails to produce the theoretically expected amine:

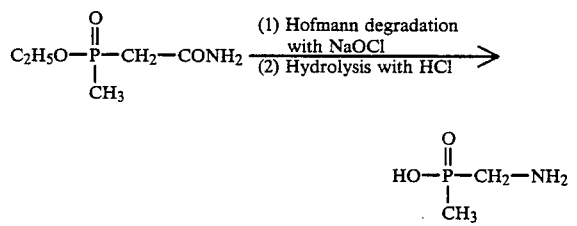

In the attempt to modify the reactions described by M. Soroka and P. Mastalerz in the cited place (shown above under (c), (d) and (e)) in a manner such that the normal halogen-free Hofmann degradation products (α-aminoalkylphosphonic acids) are also produced with high yields in those reactions, and also in the attempt to extend these reactions if required in addition to other similar P-C compounds, it was then found that this object is achieved in a process wherein the starting point is not the esters of the corresponding aminocarbonylalkylphosphonic acids (M. Soroka and P. Mastalerz in the above cited place!), but the respective ester salts. In the aminocarbonylalkylphosphinic acid series the reaction can be achieved in a similar manner with aminocarbonylalkylphosphinic acid salts as starting compounds.

The subject of the invention is therefore a process for the preparation of α-aminoalkylphosphonic and of α-aminoalkylphosphinic acids of the formula I

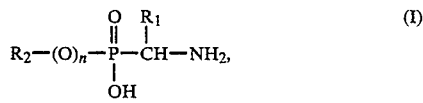

where n = 1 or 0, $R_1$=H, $CH_3$ or $CH_2-C_6H_5$, and $R_2$=H (for n =1) and also = alkyl or phenyl (for n =0), wherein compounds of the formula II

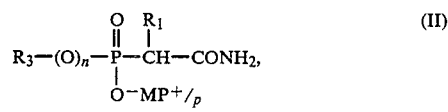

where n and $R_1$ have the same meaning as in formula I, $R_3$= alkyl (for n =1), = alkyl or phenyl (for n =0), and $M^{p+}$ = p-valent cation, are subjected to a Hofmann degradation and the compounds of formula I are obtained in the known manner.

The yields of α-aminoalkylphosphonic and α-aminoalkylphosphinic acids of formula I are in this case without exception between about 70 and 90% of theoretical. This is extremely surprising since according to M. Soroka and P. Mastalerz and also according to our own experiments mentioned above mainly halogenated phosphonic and phosphinic acid derivatives and virtually no normal halogen-free Hofmann degradation products (amines) are obtained by Hofmann degradation and acidic hydrolysis of compounds of formula II in fully esterified form. The relatively insignificant modification of the starting compounds (ester salts or salts instead of only the ester) did not in any way allow the quite different reaction (according to the invention) to be expected.

In formula II for the starting compounds $R_1$ preferably stands for H or $CH_3$, and $R_3$ stands for a $C_1$-$C_8$, preferably a $C_1$-$C_4$, alkyl radical, in particular only the $C_2H_5$ radical (for n =1) or a $C_1$-$C_8$, preferably a $C_1$-$C_4$ alkyl radical (for n =0);

$M^{p+}$ preferably stands for $Na^+$ or $K^+$ (p =1).

For n =1 in the case of the compounds of formula II the ester salts of aminocarbonylalkylphosphonic acids (IIa) are represented:

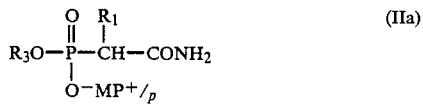

They can be obtained by processes known from the literature, e.g. by reaction of esters of phosphorous acid esters with α-halo carboxylic acid amides (for example as in J. Org. Chem. 23, pages 1883–1886 (1958)) followed by partial saponification:

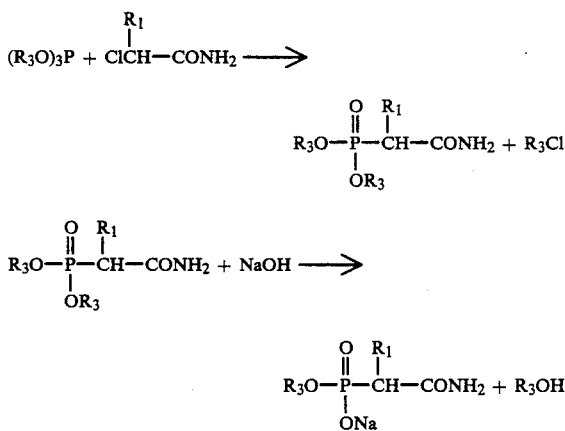

The partial saponification is normally carried out by reaction with a metal hydroxide, preferably with Na or K hydroxide in aqueous or alcoholic solution.

For n =0 the compounds of formula II are salts of the amino-carbonylalkylphosphinic acids (IIb):

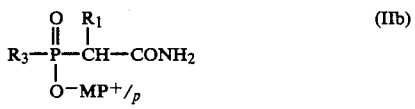

Their preparation is also carried out by known processes, e.g. analogously to the abovementioned preparation of the ester salts of aminocarbonylphosphonic acid:

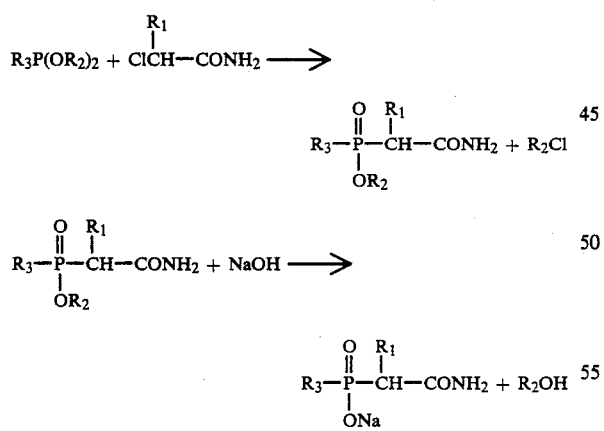

The Hofmann degradation of the compounds of formula II (by means of chlorine or bromine/alkali hydroxide) is carried out as is usual and known for this type of reaction.

Preferably the procedure is that an alkaline hypohalogenite solution is first prepared by a reaction of chlorine or bromine in an alkali hydroxide solution. The compound II is introduced into this solution either in solid form or as an aqueous solution at about 10 to 20° C. The halogen: alkali hydroxide: compound II molar ratio is expediently about (1 to 1.2): about (4 to 6): about 1.

After the addition of the compound II the temperature is advantageously raised for about 30 to 90 minutes, preferably about 30 to 40 minutes, to about 50 to 90° C., preferably to about 60 to 75° C.

The working up of the reaction solution obtained is carried out in a manner known per se. For example, to liberate the α-aminoalkylphosphonic or α-aminoalkylphosphinic acid (I) reaction is carried out with acids. In the case of the preparation of α-aminoalkylphosphonic acids (compounds of the formula I with n =1) this is carried out, for example, by acidifying with hydrochloric acid and heating for about 2 to 4 hours at elevated temperature, preferably at the boiling point of the reaction medium (reflux).

In the case of the preparation of the α-alkylaminophosphinic acids (compounds of the formula I with n =0) acidification is also carried out expediently with hydrochloric acid, but in this case no heating is necessary.

The isolation of end product I is then carried out (after the separation of the alkali halide also produced) by known methods. Preferably, the isolation is carried out by concentrating the hydrochloric acid solution by evaporation and a reaction of the hydrochlorides obtained in alcoholic solution with ethylene oxide, propylene oxide or a weak organic base such as, for example, pyridine.

The invention is now explained in more detail by the following examples. The invention examples (A) are followed by two further comparative examples (B) from which it is evident that under the conditions of the Hofmann degradation virtually no aminomethanephosphonic acid or aminomethyl methylphosphinic acid is produced from diethyl aminocarbonylmethylphosphonate and ethyl aminocarbonylmethyl methylphosphinate respectively.

(A) INVENTION EXAMPLES

Example 1

Aminomethanephosphonic acid

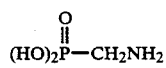

(a) Preparation of the starting compound, sodium salt of monoethyl aminocarbonylmethylphosphonate

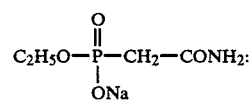

Diethyl aminocarbonylmethylphosphonate was obtained from triethyl phosphite and chloroacetamide in the known manner by the Arbusov method.

48.0 g (1.2 mol) of sodium hydroxide were added to a solution of 195.2 g (1 mol) of diethyl aminocarbonylmethylphosphonate in 500 ml of absolute ethanol cooled to −15° C. The solution, which heated up to 65° C., was stirred without cooling for 3.5 hours. The precipitated product was then filtered off by vacuum and washed with ether. 156 g (80%) of the sodium salt of monoethyl aminocarbonylmethylphosphonate were obtained.

(b) Reaction according to the invention:

A solution of 75.6 g (0.4 mol) of the sodium salt of monoethyl aminocarbonylmethylphosphonate in 100 ml of water was added at room temperature to a hypochlorite solution prepared at 0° C. from 67.2 g (1.68 mol) of sodium hydroxide, 29.8 g (0.42 mol) of chlorine and 400 ml of water.

After 15 minutes, heating at 75° C. was carried out for 30 minutes and hydrogen chloride was introduced until saturation was reached. The reaction solution was heated for 2 hours under reflux. After cooling down to 10° C., 108 g of sodium chloride were filtered off. The filtrate was evaporated to dryness, mixed with 150 ml of concentrated hydrochloric acid and a further 13 g of sodium chloride were filtered off.

Evaporation was again carried out to dryness and 200 ml of methanol and 30 ml of pyridine were added. 32 g (72%) of aminomethanephosphonic acid were obtained.

EXAMPLE 2

(Aminomethyl)methylphosphinic acid

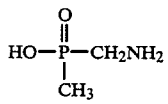

(a) Preparation of the starting compound sodium (aminocarbonylmethyl)methylphosphinate

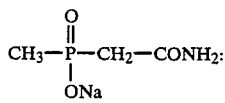

(a) (Aminocarbonylmethyl)methylphisphonic acid was prepared in the usual manner from diethyl methanephosphonite and chloroacetamide.

Sodium (aminocarbonylmethyl)methylphosphinate was obtained by reaction with sodium hydroxide analogously to Example 1.

(b) Reaction according to the invention: A solution of 63.6 g of sodium (aminocarbonylmethyl)methylphosphinate in 50 ml of water was added at room temperature to a hypochlorite solution prepared as in Example 1.

The temperature was kept at 20° C. for 15 minutes and the heating was carried out for 30 minutes at 60° C. After acidification of the reaction solution through the introduction of hydrogen chloride, evaporation to dryness was carried out, 200 ml of methanol were added and the sodium chloride (112 g) was filtered off by vacuum.

24 g of propylene oxide were added to the methanol solution and the precipitated product was filtered off by vacuum. 35 g (80%) of (aminomethyl)methylphosphinic acid were obtained.

EXAMPLE 3

1-Aminoethanephosphonic acid

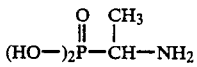

(a) Preparation of the starting compound, sodium salt of
monoethyl 1-aminocarbonylethylphosphonate

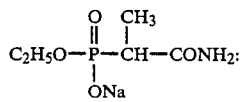

Diethyl 1-aminocarbonylethylphosphonic acid was obtained by a procedure given in the literature (J. Am. Chem. Soc. 79, 1963 (1957)) from triethyl phosphite and ethyl 2-bromopropionate with subsequent ammonolysis. 17.6 g (0.44 mol) of sodium hydroxide were added to a solution of 83.7 g (0.4 mol) of diethyl 1-aminocarbonylethylphosphonate in 150 ml of absolute ethanol. The solution, which heated up to 35° C., was boiled under reflux for one hour. After cooling down, the precipitated product (60.3 g equivalent to 74% yield) was filtered off and washed with ether.

(b) Reaction according to the invention: 61 g (0.3 mol) of the sodium salt of monoethyl 1-aminocarbonylethylphosphonate were added at room temperature to a hypochlorite solution prepared at 0° C. from 52.8 g (1.32 mol) of sodium hydroxide, 22 g (0.31 mol) of chlorine and 300 ml of water. After 15 minutes heating was carried out for 30 minutes at 70° C., cooling was carried out to 20° C and acidification was carried out with concentrated hydrochloric acid. After evaporation to dryness, 80 ml of concentrated hydrochloric acid were added, the insoluble sodium chloride (94 g) was filtered off and the filtrate was boiled for 2 h under reflux. The reaction solution was concentrated by evaporation and were added 100 ml of methanol and 25 ml of pyridine. 33 g (88%) of 1-aminoethanephosphonic acid were obtained.

(B) COMPARATIVE EXAMPLES

COMPARATIVE EXAMPLE 1:

Experiment on the Hofmann degradation of diethyl aminocarbonylmethylphosphonate

78 g (0.4 mol) of diethyl aminocarbonylmethylphosphonate were added at room temperature to a hypochlorite solution at 0° C. from 67.2 g (1.68 mol) of sodium hydroxide, 29.8 g (0.42 mol) of chlorine and 400 ml of water. The solution, which first heated up to 50° C. without heating, was heated for 30 minutes at 65° C. and acidified with concentrated hydrochloric acid after cooling down. After evaporation on a rotary evaporator 150 ml of concentrated hydrochloric acid were added, the common salt formed was filtered off, and the filtrate was heated for 2 hours under reflux. After complete evaporation 200 ml of methanol and 30 ml of pyridine were added. A precipitation of the aminomethanephosphonic acid, which is insoluble under these conditions, was not observed. In addition only traces of aminomethanephosphonic acid could be detected in the thin-layer chromatogram.

COMPARATIVE EXAMPLE 2:

Experiment on the Hofmann degradation of ethyl (aminocarbonylmethyl)methylphosphinate

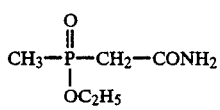

In the reaction of 66 g (0.4 mol) of ethyl (aminocarbonyl methyl)methylphosphinate under conditions identical to the Comparative Example 1 it was not possible to detect any trace of (aminomethyl)methylphosphinic acid in the methanol solution obtained during working up.

I claim:

1. A compound of formula II

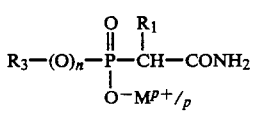

wherein
n is 1 or 0,
$R_1$ is H, $CH_3$ or $CH_2-C_6H_5$,
$R_3$ is $C_1-C_8$-alkyl when n is 1, and $C_1-C_8$-alkyl or phenyl
when
n is 0, and
$M^{p+}$ is $Na^+$ or $K^+$.

2. A compound as claimed in claim 1, wherein $R_3$ is $C_1-C_4$-alkyl.

3. A compound as claimed in claim 1, wherein n is 1.

4. A compound as claimed in claim 1, wherein $R_1$ is H.

5. A compound as claimed in claim 1, wherein $R_1$ is $CH_3$.

6. A compound of formula III

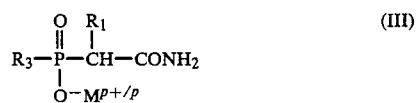

wherein
$R_1$ is H, $CH_3$ or $CH_2-C_6H_5$,
$R_3$ is $C_1-C_8$-alkyl or phenyl and
$M^{p+}$ is $Na^+$ or $K^+$.

7. A compound as claimed in claim 6, wherein $R_3$ is $C_1-C_4$-alkyl.

8. A compound as claimed in claim 6, wherein $R_1$ is H.

9. A compound as claimed in claim 6, wherein $R_1$ is $CH_3$.

10. A compound of formula IV

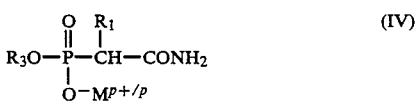

wherein
$R_1$ is H or $CH_2-C_6H_5$,
$R_3$ is $C_1-C_8$-alkyl and
$M^{p+}$ is $Na^+$ or $K^+$.

11. A compound as claimed in claim 10, wherein $R_1$ is H.

12. A compound as claimed in claim 11, wherein $R_3$ is $C_1-C_4$-alkyl.

* * * * *